United States Patent [19]
Mixon, Jr.

[11] 4,254,767
[45] Mar. 10, 1981

[54] LABORATORY DEVICE FOR SMALL ANIMALS

[76] Inventor: James L. Mixon, Jr., 5129 Irene Dr., Harrisburg, Pa. 17112

[21] Appl. No.: 61,640

[22] Filed: Jul. 30, 1979

[51] Int. Cl.³ .............................................. A61M 5/00
[52] U.S. Cl. ................................. 128/216; 128/132 R
[58] Field of Search ............... 128/216, 303 R, 303 B, 128/215, 132 R; 119/103, 96, 160

[56] References Cited
U.S. PATENT DOCUMENTS

| | | | |
|---|---|---|---|
| 2,952,031 | 9/1960 | Breitkreutz | 119/96 X |
| 3,542,030 | 11/1970 | Hoffman et al. | 128/303 B |

Primary Examiner—John D. Yasko
Attorney, Agent, or Firm—Allan B. Osborne

[57] ABSTRACT

The present invention relates to a device which confines and restrains a small laboratory animal. The present invention further includes a hypodermic needle carrier which is movable in a vertical line to insert the needle into the animal's head, and further included are means for accurately positioning the needle over the point of entry.

12 Claims, 8 Drawing Figures

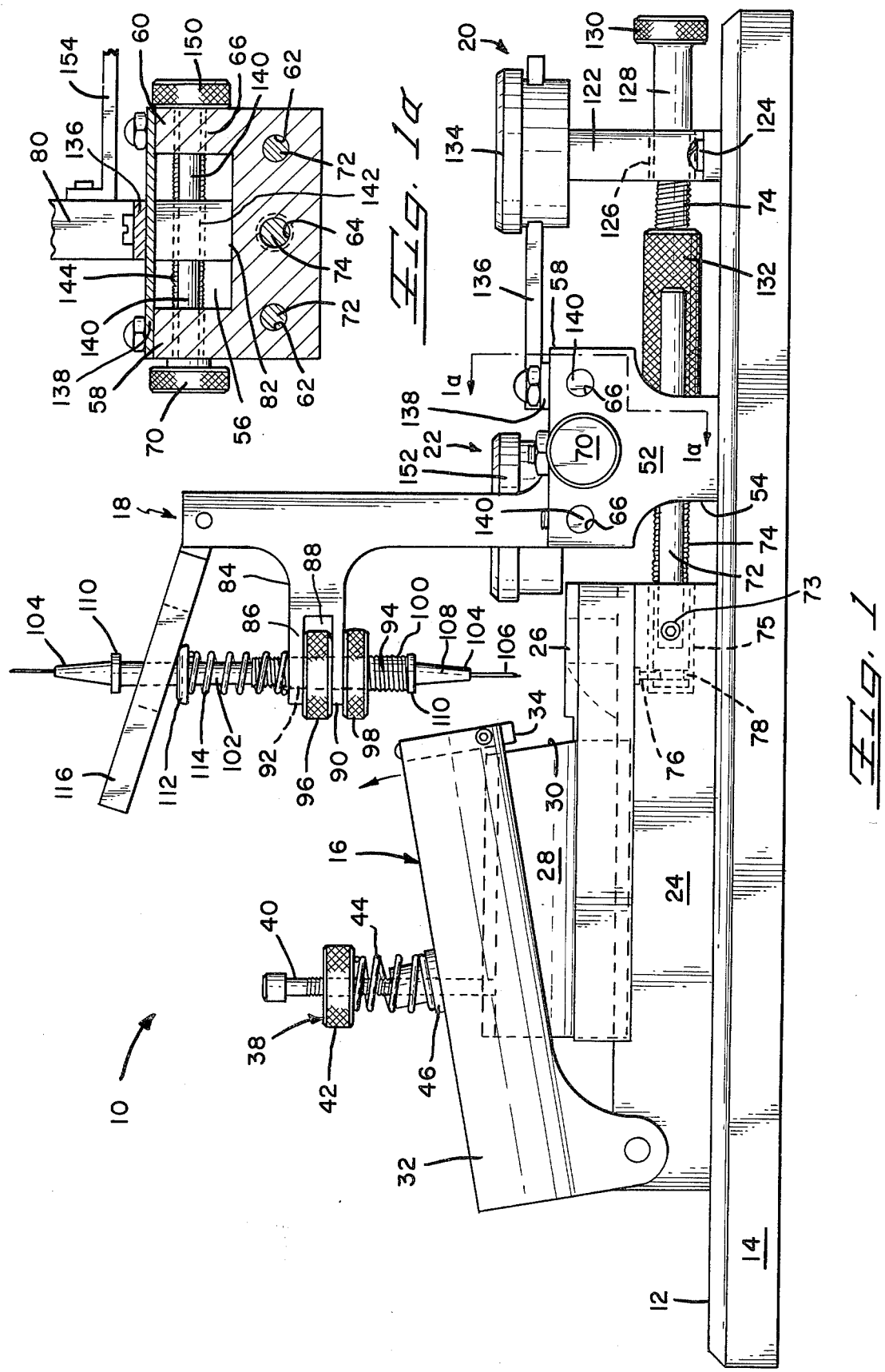

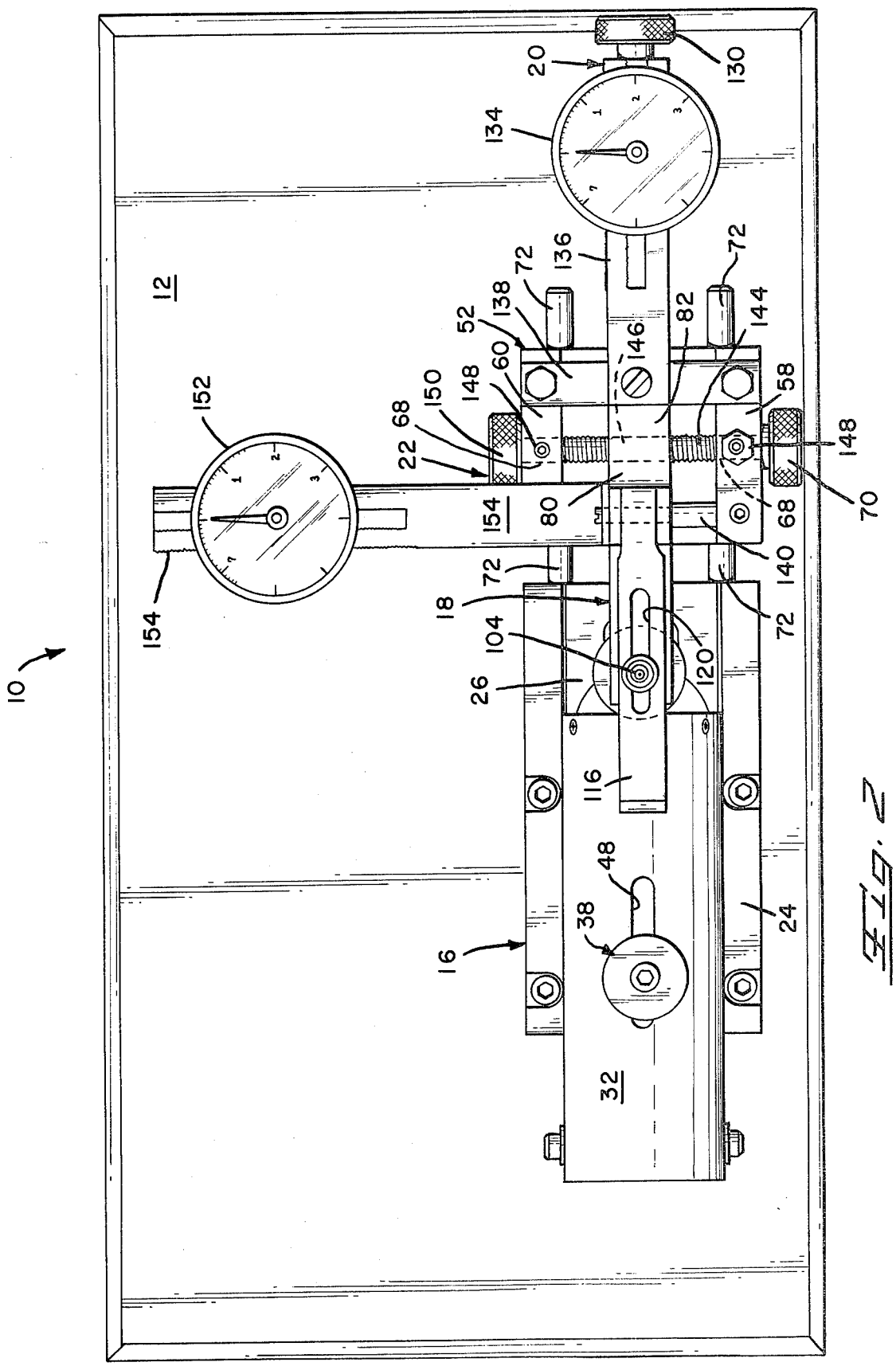

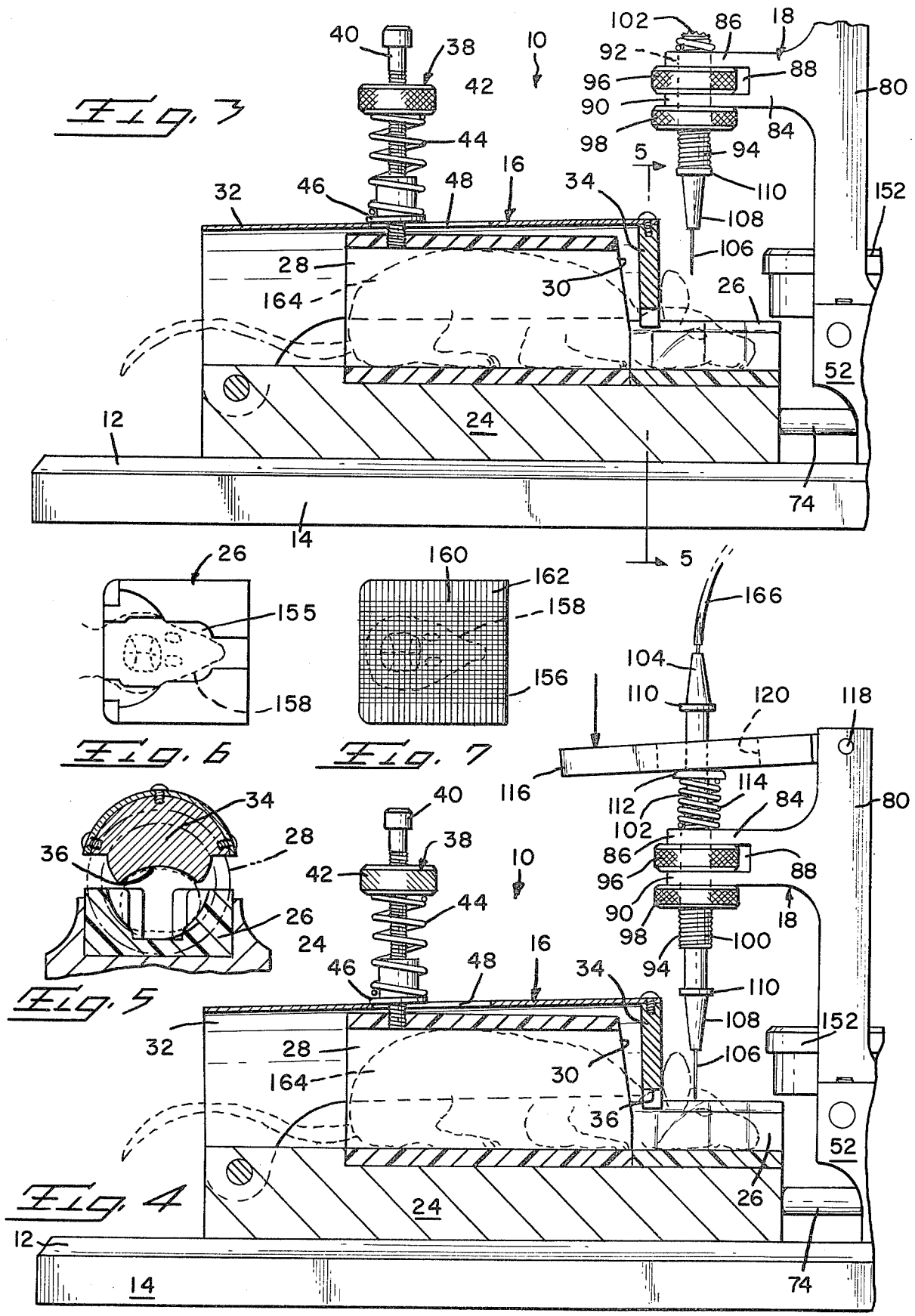

LABORATORY DEVICE FOR SMALL ANIMALS

BACKGROUND OF THE INVENTION

1. Field of the Invention

The present invention relates to small animal restraining devices for use in laboratories.

2. Prior Art

Many devices are known and used to immobilize small laboratory animals so that operations, dissections and the like may be performed thereupon. The most common devices are those which hold the entire animal in an immobile position. One such device is disclosed in U.S. Pat. No. 2,832,313. Wherein a series of elongated flexible fasteners are attached to the animal's legs. The head of the animal is held by means of a holder in which an incisor enters and is retained.

Less common are the devices which hold the animal and in particular its head under virtually no toleance for movement. These types of devices provide the means so that a cannula or needle can be inserted into the skull to hit an infinately small target with a high degree of accuracy. U.S. Pat. No. 3,542,030 discloses a device of this type. The primary means of holding the animal's head is a pair of earbars which enter the outer ears to make firm, mechanical contact with the osslus structure. These earbars can be adjusted with great precision. The earbars also provide means for guiding the insertion of a cannula to the animal's pituitary gland. Two nosebars, which are clamped across the animal's upper jaw, are fixed to a carriage which can be adjusted to move the head vertically with precision. Once this device is adjusted, it can be used on like animals having similar structural dimensions without further adjusting. In order to employ the device of this invention, however, the animal must be anesthetized. Further, the nature of the guide means limits the place in the animal's head into which the cannula may be inserted.

SUMMARY OF THE PRESENT INVENTION

The present invention provides a device which includes a base, means for restraining a laboratory animal, means for accurately moving a needle over a pre-determined point and means for driving the needle into the animal's head so that a fluid may be injected thereinto.

BRIEF DESCRIPTION OF THE DRAWINGS

FIG. 1 is a side elevation view of the device constructed in accordance with the present invention;

FIG. 1a is a view taken along lines 1a—1a of FIG. 1;

FIG. 2 is a top plan view of the device of FIG. 1;

FIGS. 3 and 4 are similar side elevation views, partially in section, showing the utility of the device;

FIG. 5 is a view taken along lines 5—5 of FIG. 3 looking into the holding portion of the animal-receiving tube;

FIG. 6 is a top plan view showing in detail the animal head holding block; and

FIG. 7 is a top plan view of a gage block.

DESCRIPTION OF THE INVENTION

Device 10, constructed in accordance with the preferred embodiment of the present invention, is seen from one side in FIG. 1. The device includes four major components, all of which are mounted, directly or indirectly, on a brass plate 12 which in turn is secured to the surface of a wooden base 14. The four major components are the animal restraint assembly 16, needle rod assembly 18, X-adjustment unit 20 and Z-adjustment unit 22.

Animal Restraint Assembly

At least one of the novel features of the restraint assembly herein below described, is that it induces the animal to seek sanctuary within a tunnel and then, once inside, the animal's head is easily and completely immobilized. There is no need whatsoever to anesthetize nor tranquilize the animal before hand.

The subject assembly is mounted on an easily removable support block 24 which is preferably of metal. A squarish head block 26 is positioned in a cavity at the front end of the support block. The details of the head block will be discussed below. Directly behind the head block and mounted on block 24 is tunnel tube 28 which may be of any material including for example, lucite. The upper section of the tube's front opening may be beveled as shown and indicated by reference numeral 30. Tube 28 extends rearwardly for a pre-determined distance.

The hold down member, indicated by reference numeral 32, is pivotally mounted at the back of support block 24. This member is an elongated, generally U-shaped shell with its axial opening facing the block so that it can be moved down over tube 28 in a tight fit as shown in FIGS. 3 and 4. The shell's interior dimensions and shape corresponds very closely or exactly with the tube's outer configuration to prevent misalignment and lateral play.

The back end of the shell is open while a neck-engaging plate 34 is secured across the upper section of its front-end opening. The lower edge of the plate, indicated by reference numeral 36 in FIG. 5, is arcuate-shaped so as to conformably fit across thhe animal's neck and against the rear portion of its skull.

A hold-down adjustment subassembly, indicated by reference numeral 38 in FIG. 1, consists of a partially threaded rod 40, adjustment wheel 42, coil spring 44 and slide washer 46. The rod extends thru slot 48 in shell member 32 as can be seen in FIG. 2. It's lower end is fixed to tube 28. The slide washer and coil spring are positioned between the shell and the adjustment wheel 42 which is threaddedly engaged on the rod adjacent its upper end. The subassembly provides the means for applying the desired amount of pressure on the animal's neck by adjusting the tension in spring 44 in the conventional manner.

The details of head block 26 can be seen in FIG. 6. The block is hollowed out to conformably receive the animal's head. Although not shown, the forward end of the hollowed-out portion can be provided with a crossbar or some similar device on which the animal can grasp with his teeth.

Dimensions of the several parts making up the animal restraint assembly has not been given for the reason that this assembly can be tailor made to a particular kind of animal. The remaining components of device 10, as will be seen, are independently functional irrespective of the size or kind of animal. Accordingly, device 10 is suited for different kinds of animals by simply replacing parts of or the complete animal restraint assembly. Thus a laboratory can have on device 10 with several different-sized animal restraint assemblies mounted on separate support blocks 24 and thus have the versatility of working on several different sizes and kinds of animals without the expense of several devices 10.

Traveling Block

The afore-described animal restraint assembly is, relative to the other components of device 10, stationary. Its principal function is to restrain and hold the head of a laboratory animal motionless so that a hypodermic needle may be inserted into a selected area in the animal's brain and a fluid injected for laboratory experiments. In that the targets are very tiny, the needle must be moved in the X, Y and Z directions with extreme accuracy; e.g. within 0.05 mm. To accomplish this, the several parts must be machined to precision tolerance. Further, the needle's vertical travel must also be straight; i.e., it absolutely cannot deviate during its vertical travel.

As noted above, there are four major components: animal restraint assembly, needle-rod assembly, and the X and Z adjustment assemblies. The latter three components include the means to position a needle so that it will enter the animal's head at a precise point. The keystone of these three units is traveling block 52 which will now be described with reference principally to FIG. 1a but also to FIGS. 1 and 2.

In the main, block 52 is rectangular. To accomodate certain bushings, the lower portion of the block is smaller in length, from front to back as indicated by reference number 54 in FIG. 1. On the block's upper surface a channel 56 is provided, also extending from front to back. Side walls 58 and 60 define and bracket the channel for the full length of the block.

There are three holes extending thru the lower portion of the block from front to back. Two of the holes designated by reference numeral 62, are near the block's left and right sides and are positioned approximately below side walls 58 and 60. The thrid hole, designated by reference numeral 64, extends through the block and is located between the two holes 62. This hole is internally threaded to receive threaded adjusting screw 74.

There are also three holes which extend thru both side walls 58 and 60 in a direction transverse to the first set of holes. Referring to FIG. 1, one can see two holes, indicated by reference numeral 66, near the front and back ends of the block. The third hole 68, shown in phantom in FIG. 2, lies between holes 66 and is masked by adjusting wheel 70 in FIG. 1.

Traveling block 52 is preferrably machined from brass. It rests and slides on brass plate 12 in front of block 24. It is confined to reciprocal movement by two rods 72 which project forwardly from apertures in block 24 and pass thru holes 62. These rods may be clearly seen in FIG. 2. Holes 62 in block 52 may have bushings or bearings therein to facilitate the block's sliding along the rods.

Rods 72 are secured in the apertures in block 24 by set screws 73, one of which is shown in FIG. 1.

The aforementioned adjusting screw 74, which is part of X-adjustment unit, threadly passes thru traveling block 52 and is rotatably retained in an aperture in block 24 by a set screw riding in an annular groove adjacent one end of the adjusting screw. This arrangement is shown in phantom in FIG. 1 wherein reference numeral 75 points out the adjusting screw receiving aperture, reference numeral 76 points out the set screw and reference numeral 78 points out the groove. Although its not obvious, the portion of adjusting screw 72 which resides in aperture 75 is not threaded and the fit between the aperture surface and the screw is very close.

Needle Rod Assembly

Needle rod assembly 18 is positioned on traveling block 52 and more particularly in channel 56 of that block. This assembly includes vertical support member 80 whose lower end 82 rides or slides on the channel's floor as can be seen in FIG. 1a.

Returning to FIG. 1, at about two-thirds of the distance upwards on the support member, horizontal arm 84 projects rearwardly. The free end of this arm is notched to provide a horizontal upper bar 86, slot 88 and a horizontal lower bar 90.

Vertical holes 92, shown in phantom in FIG. 1, are provided thru both bars in aligned relation. A needle rod housing 94 is movably positioned in the holes with the ends thereof preferably extending above and below the two bars 86 and 90.

The needle rod housing further passes thru a central opening (not shown) in adjusting wheel 96, located in slot 88 and locking wheel 98, located below bar 90. The openings in both wheels are threaded (not shown) and conformably engage the exterior threads 100 on the housing. With the locking wheel backed off away from lower bar 90, the needle rod housing may be moved up or down by rotating adjusting wheel 96. The housing may be locked in a pre-determined position by running locking wheel 98 up against the lower bar.

With continuing reference to the extreme accuracy required, the housing, the holes in the bars, the adjusting and locking wheels and the associated threads all must be machined with great precision so that the housing cannot be inadvertently moved in any direction.

Needle rod 102 is slidably positioned in housing 94. The fit therein between is glove-like with just enough clearance to allow the rod to be moved up and down in the housing without deviation from its vertical path. A passage (not shown) extends thru the rod with openings at both ends. The ends are tapered to receive a disposal needle 104 thereon. Each needle consists of a conventional hypodermic-type needle 106 fixed to a cone-shaped sleeve 108. A laterally projecting flange 110 is present on the sleeve top. As FIG. 1 shows, the sleeve is simply slipped on over the rod's tapered end. After use, the needle and sleeve is removed and thrown away.

A rubber tube (FIG. 5) leads from a syringe (not shown) to the needle on the rod's upper end. Fluid from the syringe passes thru the rod's passage and thru the needle on the rod's lower end.

An annular upset 112 is located on and is a fixed integral part of needle rod 102. As shown in FIG. 1, the upset is located about a third of the way down from the top of the rod. The top surface is curved and its lower surface is flat. A coil spring 114, surrounding the needle rod, is retained by and between the flat surface of the upset and the upper horizontal bar 86. The spring biases the rod in a up or 'rest' position.

A lever 116, pivotally mounted to support member 80 in its upper, forked end by pin 118, extends rearwardly. The lever has a vertically extending slot 120 (FIG. 2), shown in phantom in FIG. 1, thru which passes the upper part of needle rod 102. By reason of the slot, the lever rests on the upset's curved upper surface. Upon pushing down on the free end of the lever, the needle rod is moved downwardly. Upon releasing the lever, the coil spring returns it and the rod to the rest position.

In the present embodiment, the amount of downward travel of the rod is controlled by the flat surface of the upset 112 on the needle rod coming in contact with the top surface of the needle rod housing. Other means may be employed to limit the vertical travel. For example, a gage block (not shown) may be placed between the upper horizontal bar 86 and the lever 116.

In summary, the needle rod assembly provides an adjustable means for lowering the needle through a precise distance without deflection from the vertical.

X-Adjustment Unit

The aforementioned needle rod assembly provides an extremely accurate means for moving a needle along a vertical path. The X-adjustment unit, generally indicated by reference numeral 20 in FIGS. 1 and 2, provides the means for moving the needle rod assembly via traveling block 52, back and forth along the longitudinal axis of the animal restrain assembly; i.e., this unit enables the operator to move the point of needle insertion along the length of the animal's head with extreme accuracy.

The structural units that provide the capability to adjust the needle in this direction includes vertical post 122 which is shown in FIG. 1. This post is securely fastened to the wooden base 14 thru plate 12 by means of machine screws 124 or other conventional fastening means. The post has an opening 126 therethru which is shown in phantom. This opening receives and supports knob extension 128 which is a continuation of adjusting screw 74. A knob 130 at the free end of the extension is knurled to aid in turning the screw.

A locknut 132, positioned on screw 74 may be rotated to abut against traveling block 52 to lock it in place once the desired X-axis location of the needle is obtained. With the locknut in a free position, by rotating knob 130, the screw moves traveling block 52 and the attached needle rod assembly 18 toward and away from animal restraint assembly 16. The threads on the adjusting screw are very fine to provide an incrementally small linear movement for each turn of the knob.

The amount of travel via adjusting screw 74 is observable in gauge 134 which is secured to the top of post 122. The face of the gauge; i.e., the dial and pointer, may be seen in FIG. 2. Gauge 134 is of a conventional type such as found on calipers. It is actuated by bar 136 which is secured to cross bar 138 (FIG. 2) on traveling block 52. The bar slides back and forth thru the gauge housing engaging gear wheels (not shown) which in turn moves the pointer.

Z-Adjustment Unit

The Z-adjustment unit provides the means for moving the needle rod assembly right or left with respect to the animal restraint assembly; i.e., in a direction across the X-adjustment unit axis. The principal component of the Z-adjustment unit is the needle rod assembly's support member 80 and more particularly its lower end 82 which is located in channel 56 of the traveling block. The support member 80 cannot move frontwards or backwards in the channel by reason of two rods 140 which are positioned in holes 66 in side walls 58 and 60. These rods cross the channel, passing thru holes in the support member, one of which is shown in phantom in FIG. 1a. Reference numeral 142 points out this hole. The rear rod 140 can be seen in FIG. 2 and the ends of both can be seen in holes 66 in side wall 58 in FIG. 1.

As noted above, rods 140 prevent support member 80 from moving back and forth in channel 56; they also provide guide and support means for that member moving sideways between the two side walls 58 and 60. The means for driving support member 80 sideways is adjusting screw 144 which is journaled in holes 68 (FIG. 2) in side walls 58-60 and threadly engaged in hole 146 in lower end 82 of the support member. Adjusting screw 144 and hole 146, the latter being shown in phanotm, can be seen in FIG. 2.

With continued reference to FIG. 2, set screws 148, located in side walls 58-60, intersect holes 68 and ride in grooves (not shown) in adjusting screw 144. As is known, this arrangement allows the screw to rotate while preventing it from moving axially.

The aforementioned knob 70 is an integral part of the right end of screw 144. Rotating this knob moves the support member along the screw.

Lock wheel 150 is threadly and rotatably mounted on the screw's left end. Running the wheel up against side wall 60 locks the screw and support member so as to prevent unintentional movement.

The means for determining the amount of travel in the Z direction of the support member, and needle 106, is gauge 152 which is firmly mounted to an extension of rear rod 140; i.e., the rod nearest the animal restraint assembly. A bar 154, its one end secured to the side of support member 80, (see also FIG. 1a) slides back and forth through the gauge housing, engaging gears within (not shown), to move the pointer around the dial in the gauge face. This arrangement is identical to that set forth with respect to the X-adjusting unit. The gauges, and the means for moving the pointers, are well known and do not, per se constitute a part of the present invention.

The Head Block

Head block 26 contains a cavity 155 which is shaped to conformably receive the lower half of the head of the laboratory animal. Different blocks (not shown) can be provided with cavities for different kinds and sizes of animals.

Summary

Animal restraint assembly 16 provides a means for inducing an animal into its confines and for holding its head immobile, all without injury to the animal and without need to tranquilize or anesthetize it.

Needle rod assembly 18 provides the means for moving a hypodermic-type needle through a precisely predetermined vertical distance with extremely close tolerances. The vertical distance of travel is adjustable simply and with great accuracy.

X-adjustment unit 20 provides the means for moving the needle back or forth in the X-direction with accuracy, within extremely close tolerances.

Z-adjustment unit 22 provides the means for moving the needle sideways (left or right relative to the animal's head), again with extreme accuracy.

The Gage Block

FIG. 7 is a top plan view of a block 156 of lucite in which is embedded a skull 158 of a mouse. Block 156 has the same dimensions as head block 126. Further, skull 158 occupies the same position within the block 156 that a live mouse head does in block 26.

Longitudinal lines 160 and normal lines 162 are scribed on the block's surface on one millimeter spacing vertical and horizontal lines are scribed on the sides of the block also. The block and its lines provide the laboratory worker with a method to determine how far to move the needle rod housing vertically and horizontally with the X and Z-adjustment units so that the needle 106 enters the animal's head at the precise, desired location and to the precise desired depth. This method will be discussed below.

Gage blocks containing skulls of other laboratory animals may also be provided; i.e., device 10 and its use is not restricted to mice.

A Method of Use

In preparing device 10 for use, head block 26 is temporarily replaced with gage block 156. Using the X and Z adjusting screws, needle 106 is positioned directly over the center square (not referenced) on the gage block. The pointers in gauges 134 and 152 should be pointing to the zero mark. If not, manual adjustment means generally provided on the gauges can be used to zero the pointer.

The depth that the needle is to penetrate the animal's skull is determined by moving the gage block so that the needle moves down along one side with lever 116 fully depressed, and locking wheel 98 backed away from lower bar 90, adjusting wheel 96 is rotated to move the housing, needle rod and the needle up or down to the desired depth. The locking wheel is then moved back up against the lower bar to secure the adjustment.

After the needle is centered, and with gage block 156 still in place, the operator may move the needle to overlie the target in the animal's brain. With the knowledge as to where the target is, he can move the needle to that point by rotating knobs 130 (X-adjustment) and 70 (Z-adjustment). The position of the pointers in gauges 134 and 152 may be recorded for further reference. Gage block 156 is now replaced with head block 26, tubing from a syringe or stereotoxic device mounted on base 14 (not shown) is attached to needle 104 on top of needle rod 102.

The operator, holding a mouse 164 (FIG. 3) by its tail, pivots the front of hold-down member 32 upwardly as indicated by the arrow in FIG. 1. Still holding the mouse by its tail, he moves it to the back of restraint assembly 16 so that the mouse sees tunnel tube 28. Believing this to be a sanctuary, the mouse scampers in. As soon as its head emerges from the tube's front opening (encouraged if necessary to do so by gentle pressure from the operator) the hold-down member is allowed to move down over the tube. The neck engaging plate 34 catches the mouse immediately behind its head and forces it into cavity 155 in head block 26. FIG. 3 shows the mouse so restrained. Pressure on the mouse is provided by the coil spring 44 in the hold-down adjustment subassembly 38. If additional pressure is required, the operator rotates wheel 42 to shorten the spring length.

With the mouse immobilized, the operator fully depresses lever 116 as shown in FIG. 4. Holding the lever down, fluid is injected through needle 106 into the animal's brain at the selected location. The tubing carrying the fluid from the syringe is shown in FIG. 4 and is indicated by reference numeral 166.

After the proper amount of fluid has been injected, the operator releases lever 116. Coil spring 114 returns the needle rod assembly to its rest position. The operator pivots the hold-down member 32 upwardly and mouse 164 is removed. A second mouse may now be introduced into the tunnel tube to repeat the process. In that the needle is in the determined position, as many mice can be treated as desired simply by depressing the lever each time a new mouse is in place; i.e., there is no need to make an adjustment each time.

In the event some mice are to receive two injections at different locations, the operator can determine the "coordinates" before hand as outlined above. After the first injection, he simply turns the X and Z adjusting knobs to move the needle to the second location, administers the injection and readjusts the needle position, all without guess work or meticulous measurements.

One of the novel features of device 10 is that the entire animal's head is unobstructed and can be reached with needle 106 accurately.

The foregoing detailed description has been given for clearness of understanding only, and no unnecessary limitations should be understood therefrom, as some modifications will be obvious to those skilled in the art.

What is claimed is:

1. A device for use with laboratory animals comprising:
   a. restraint means to confine and restrain the animal comprising an elongated tube, opened at both ends and into which the animal can enter, and a generally U-shaped shell opened at both ends, pivotally attached adjacent to the rear end of the tube and adapted to be rotated down over the tube and a clamping member fixed to the front end of the shell which extends forwardly of the front end of the tube and having a downwardly facing, arcuate-shaped surface which is placed against the nape of the animal's neck immediately behind its head; and
   b. support means for a needle assembly on which a hypodermic-type needle may be removably placed, said support means including means to move the needle downwardly into the animal's head so that fluid may be injected thereinto.

2. The device of claim 1 further including a member having a rearwardly and upwardly opening, cavity adapted to conformably receive the lower half of the animal's head when the animal is restrained in the restraint means.

3. The device of claim 1 further including adjustable biasing means cooperating with and between the tube and shell so that varying degrees of pressure may be exerted against the animal's nape by the clamping member.

4. The device of claim 1 wherein said support means includes a vertical support member having an arm extending horizontally therefrom with its free end spaced above and in general alignment with the head of the animal which may be restrained in said restraint means, a needle rod housing movably mounted vertically thru the horizontal arm's free end, adjusting menas for adjusting the vertical positioning of the housing, a hollow needle rod slidably positioned thru the housing, said rod being adapted to receive the removable needle at its lower end and to transmit fluid therethru, and means to move the needle rod downwardly, to push the needle into the animal's head.

5. The device of claim 4 further including a block positioned in front of the restraint means and movable towards and away therefrom, said vertical support means mounted on the block's upper surface so that the needle thereon may be moved axially along the animal's head which may be restrained in the restraint means.

6. The device of claim 5 further including means to move the vertical support member back and forth across the surface of the block in a direction normal to the restraint means' longitudinal axis .

7. A device for use with laboratory animals, comprising:
   a. a base;
   b. an animal restraint assembly mounted on the base and comprising a tube and a U-shaped shell, said tube being open so that an animal may be inserted into the first end and his head may extend out of the second end, said shell being pivotally mounted adjacent the first end of the tube and adapted to be moved down over the tube with the front end extending beyond the second end of the tube, said shell having clamping means on the front end adapted to bear against the nape of an animal which may be positioned in the assembly;

c. a head block positioned on the base in front of the second end of the tube, said head block having a rearwardly and upwardly opened cavity adapted to conformably receive the lower portion of an animal's head;

d. a traveling block mounted on the base in front of the head block and movable towards and away therefrom, said traveling block having a channel extending longitudinally on its upper surface with a pair of spaced apart rails crossing the channel;

e. means for moving said traveling block;

f. a vertical support member with one end mounted on the rails and adapted to be moved back and forth across the channel thereon and the other end extending upwardly and having an arm attached thereto, said arm extending over the head block;

g. means for moving the vertical support member back and forth across the channel;

h. needle holding means mounted on the arm and adapted to be moved vertically;

i. means for moving the needle holding means vertically; and j. a hypodermic-type needle mounted in said needle holding means, one end of the needle adapted to receive fluid and the other end adapted to be driven into an animal's head upon moving the needle holding means downwardly so that the fluid may be injected into the head through the needle.

8. The device of claim 7 further including biasing means for biasing the shell downwardly over the tube.

9. The device of claim 7 wherein the clamping means include a plate having a downwardly facing concave surface.

10. The device of claim 7 further including adjusting means to adjusting the needle holding means vertically relative to the arm.

11. The device of claim 7 further including a gage block adapted to replace the head block, said gage block having embedded therein a skull of a laboratory animal and further having longitudinal and normal lines scribed on the upper surface whereby the vertical support member may be aligned so that the needle enters an animal's head at a precise, predetermined location.

12. The gage block of claim 11 further including horizontal lines scribed on one side thereof whereby the needle holding means may be adjusted so that needles may be driven into an animal's head to a precise, predetermined depth.

* * * * *